United States Patent [19]

Ohorodnik et al.

[11] 4,062,888
[45] Dec. 13, 1977

[54] CONTINUOUS PRODUCTION OF 2,5-DIOXO-1-OXA-2-PHOSPHOLANES

[75] Inventors: Alexander Ohorodnik, Erfstadt-Liblar; Elmar Lohmar, Rodenkirchen; Klaus Gehrmann, Erfstadt-Lechenich; Paul Stutzke, Walberberg, all of Germany

[73] Assignee: Hoechst Aktiengesellschaft, Knapsack near Cologne, Germany

[21] Appl. No.: 703,174

[22] Filed: July 7, 1976

[30] Foreign Application Priority Data

July 12, 1975 Germany ............................ 2531238

[51] Int. Cl.$^2$ .......................... C07F 9/02; C07F 9/28; C07C 51/54
[52] U.S. Cl. ............................ 260/545 P; 260/543 P
[58] Field of Search ..................................... 260/545 P

[56] References Cited

PUBLICATIONS

Khairullin et al., "Zhur Obsch Khm", vol. 38, No. 2, pp. 288-292, (1968).
Khairullin et al., "Zhur Obsch Khm", vol. 37, No. 3, pp. 710-714, (1967).
Khairullin et al., "Iso. Akad. Mauk. USSR, Ser. Khm", 1969, (5), pp. 1166-1168.

Primary Examiner—Norman Morgenstern
Attorney, Agent, or Firm—Connolly and Hutz

[57] ABSTRACT

Continuous production of 2,5-dioxo-1-oxa-2-phospholanes of the general formula

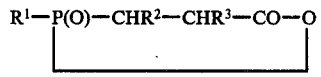

from a beta-halogenoformyl-ethyl phosphinic acid halide of the general formula

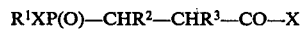

in which formula $R^1$ stands for an alkyl radical having 1, 2, 3 or 4 carbon atoms, or a phenyl radical, $R^2$ and $R^3$ each stands for hydrogen or $CH_3$, and X stands for chlorine or bromine, by reacting the said acid halide with acetic anhydride. The phospho lanes are produced by introducing, into a heatable circulation reactor, an initial quantity of the desired 2,5-dioxo-1-oxa-2-phospholane and circulating it therein at a temperature of 110° to 190° C; separately preheating the respective beta-halogenoformyl-ethyl phosphonic acid halide and acetic anhydride starting materials to a temperature of 60° to 160° C; mixing these starting materials together and continuously adding the resulting mixture to the material circulated in the reactor, the mixture being introduced into the lower third of the reactor; distilling off resulting acetyl halide near the head of the circulation reactor, a pressure difference 0.1 to 5 bar being established between the point of introduction of the mixture of starting materials and the overflow level in the circulation reactor, and the material being kept circulating by the evaporating acetyl halide; and removing the resulting desired 2,5-dioxo-1-oxa-2-phospholane from the reactor at a location which is below that at which the acetyl halide is distilled off.

1 Claim, 1 Drawing Figure

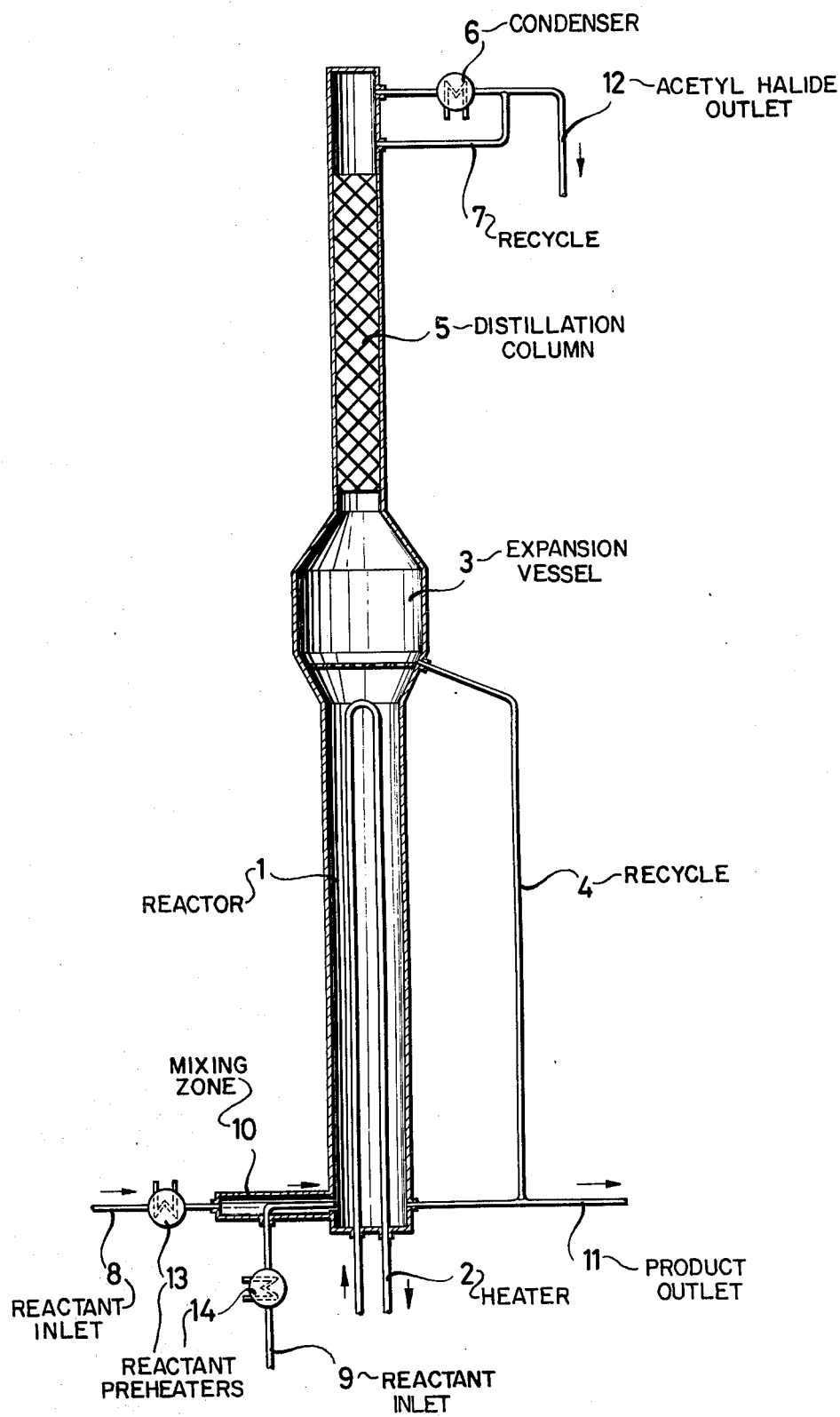

CONTINUOUS PRODUCTION OF 2,5-DIOXO-1-OXA-2-PHOSPHOLANES

This invention relates to the continuous production of 2,5-dioxo-1-oxa-2-phospholanes of the formula:

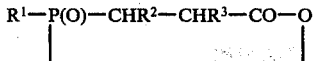

from the respective beta-halogenoformyl-ethyl phosphinic acid halides of the formula:

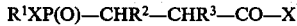

in which formulae $R^1$ stands for an alkyl radical having 1, 2, 3 or 4 carbon atoms, or a phenyl radical, $R^2$ and $R^3$ each stand for hydrogen or $CH_3$, and X stands for chlorine or bromine, by reacting the respective acid halide of the above-mentioned formula with acetic anhydride.

Various processes employing the reaction indicated above, wherein one molecule of the phosphinic acid halide in question and one molecule of acetic anhydride react to give one molecule of the phospholane in question and two molecules of acetyl chloride or bromide, have already been described.

2-methyl-2,5-dioxo-1-oxa-2-phospholane and acetyl chloride have been formed, for example, from beta-chloroformyl-ethyl methyl phosphinic acid chloride and acetic anhydride at 55° C, in a yield of 84.3% of the theoretical (cf. Z. Obsc. Chim. 37 (1967), pages 710–714).

2,4-dimethyl-2,5-dioxo-1-oxa-2-phospholane can be obtained from beta-chloroformyl-beta-methyl-ethyl methyl phosphinic acid chloride at 60° C, in a yield of 78.6% of the theoretical (cf. Z. Obsc. Chim. 38 (1968). pages 288–292). A still further process has been described, wherein 2,3-dimethyl-2,5-dioxo-1-oxa-2-phospholane is produced from beta-chloroformylalpha-methyl-ethyl methyl phosphinic acid chloride at 60° C in a yield of 69% of the theoretical (cf.Isv. Akad. Nauk, USSR. Ser. Khim 1969 (5), pages 1166–1168).

One of the advantageous uses of 2,5-dioxo-1-oxa-2-phospholanes is their condensation with polyester forming reactants with a view to the production of filaments, fibres, sheets and articles having particularly good flame-retardant or self-extinguishing properties (cf. German Published Patent Specification ("Offenlegungsschrift") No. 2346787).

By a procedure as described in the prior art, 2-methyl-2,5-dioxo-1-oxa-2-phospholane, for example, can be prepared by admixing 1 mol of acetic anhydride dropwise at 55° C with 1 mol of beta-chloroformyl-ethyl methyl phosphinic acid chloride, and keeping the resulting mixture at 55° C for 1 hour. Following this, there are distilled off first the acetyl chloride formed, next unreacted acetic anydride together with other low-boiling compounds, and finally the phospholane, at 149°–150° C under 0.5 mm Hg. The phospholane so obtained has a melting point of 97°–98° C. Experience has shown, however, that the distilled phospholane still contains acetic anhydride.

The above known processes are not fully satisfactory in two respects. Thus, firstly, the yields are unsatisfactory; and, secondly, the phospholanes obtained fail to have the purity necessary for their use as flame-retardant agents in polyester production.

According to the present invention, we provide a process for the continuous production of a 2,5-dioxo-1-oxa-2-phospholane of the general formula

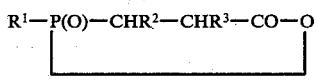

from a beta-halogenoformyl-ethyl phosphinic acid halide of the general formula

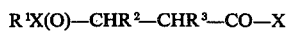

in which formulae $R^1$ stands for an alkyl radical having 1, 2, 3 or 4 carbon atoms, or a phenyl radical, $R^2$ and $R^3$ each stands for hydrogen or $CH_3$, and X stands for chlorine or bromine, by reacting the said acid halide with acetic anhydride; which process compromises introducing, into a heatable circulation reactor, an initial quantity of the desired 2,5-dioxo-1-oxa-2 phospholane and circulating it therein at a temperature of 110° to 190° C, preferably 120° to 160° C; separately preheating the respective beta-halogenoformyl-ethyl phosphinic acid halide and acetic anhydride starting materials to a temperature of 60° to 160° C, preferably 70° to 120° C; mixing these starting materials together and continuously adding the resulting mixture to the material circulated in the reactor, the mixture being introduced into the lower third of the reactor; distilling off resulting acetyl chloride or bromide near the head of the circulation reactor, a pressure difference of 0.1 to 5 bar, preferably 0.1 to 1 bar, being established between the point of introduction of the mixture of starting materials and the overflow level in the circulation reactor, and the material being kept circulating by the evaporating acetyl chloride or bromide; and removing the resulting desired 2,5-dioxo-1-oxa-2-phospholane from the reactor at a location which is below that at which the acetyl chloride or bromide is distilled off.

We have found that the adverse effects commonly encountered with the known processes mentioned earlier can be avoided to a considerable extent, provided that the desired phospholane is produced in an apparatus wherein the reaction concerned can proceed under optimum conditions. The present process is based upon the principle of preheating the respective phosphinic acid halide and acetic anhydride to such an extent that the reaction between them will occur spontaneously upon these two starting materials being injected into, and mixed together in, a mixing zone.

Since two mols of low-boiling acetyl halide, which is evaporated, are being formed per mol of phospholane, the reaction temperature would be liable to drop unless appropriate steps were taken to avoid this. Any drop in the reaction temperature would inevitably result in diminished conversion rates, i.e. in reduced space-time yields and product yields. In order to avoid these adverse effects, the reaction mixture is delivered from the mixing zone to an elongated circulation reactor, with relief of pressure. To this end, the material in question is admitted to the circulation reactor at a low level in the base portion of the reactor, so that the pressure exerted by the liquid material thereabove effectively inhibits the evaporation of the acetyl halide at a temperature lower than the reaction temperature. The pressure of the overlying liquid material decreases as the reaction mixture containing the acetyl halide rises in the circulation reactor, and therefore the evaporation of the acetyl halide occurs at a rate increasing with a decreasing pressure of the overlying liquid material. At the surface of the liquid material (overflow level) in the upper portion of the circulation reactor, the pressure of the overlying liquid material substantially reaches zero, i.e. the situation is most favourable for the evaporation of the acetyl halide. To make it possible to avoid any drop in the reaction temperature as a result of the evaporation of the acetyl halide, the invention provides for the loss of heat which this evaporation entails to be compensated by the use of a heatable reactor, and more particularly by the supply of heat through a heater disposed inside the reactor.

The evaporation of the acetyl halide causes the reaction mixture to be set in motion, so that quantitatively and completely reacted phospholane substantially free from acetyl halide can be removed through a recycle line. The product so obtained has a purity of approximately 99% and is suitable for a wide variety of uses.

Acetyl halide can be removed through a column mounted on top of the reactor. Both the phospholane and the acetyl halide can be obtained in almost quantitative yields.

Apart from the improved yields, the process of the present invention offers a number of technically significant advantages. The heatable reactor, for example, can additionally function as a still for the distillation of the acetyl halide. In addition, the nature of the present process is such that those steps which are necessary to enable the reaction to proceed under optimum conditions are steps which depend linearly on the dimensions of the apparatus used. In other words, it is possible to scale up the present process so that it can be carried out in apparatus of any desired capacity.

The invention will now be described more fully with reference to the accompanying drawing, the single FIGURE of which is a diagrammatic representation of an apparatus employed in a preferred version of the present process.

As can be seen, the circulation reactor forming the principal component of this apparatus comprises a wide tubular reactor 1 provided with a heater 2 and an expansion vessel 3 with a recycle line 4. The overflow level in the expansion vessel 3 is indicated by the broken line near the bottom of this vessel. Placed above the expansion vessel 3 there is a column 5 for distilling out the acetyl halide, which passes out through a condenser 6 provided with a recycle line 7. Before the reaction is started, the circulation reactor comprising the four components 1, 2, 3 and 4 is filled with acetic anhydride, or alternatively, and more preferably, with an initial quantity of the desired 2,5-dioxo-1-oxa-2-phospholane and preheated to 110° to 190° C by means of the heater 2. Next, beta-halogenoformyl-ethyl phosphinic acid halide, which is supplied through a line 8 and is preheated by means of a heater 13 to a temperature higher than its melting point, and acetic anhydride, which is supplied through a line 9 and is preheated by means of a heater 14, are continuously advanced through a mixing zone 10 towards the base portion of the tubular reactor 1, these two starting materials being used in a molar ratio of 1:1 to 1:1.25. Within the preferred temperature range, i.e. 120° to 160° C, these starting materials undergo spontaneous reaction so that 2,5-dioxo-1-oxa-2-phospholane and acetyl halide are continuously formed at the same rate as the starting materials are supplied to the reactor. Crude phospholane containing less than 1 weight % of acetyl halide is removed from the recycle line 4 through a heated pipeline 11. Acetyl halie which escapes in vapour form from the expansion vessel 3 is purified by distilling it in column 5, and continuously removed through the line 12.

The invention is further illustrated by the following Examples.

EXAMPLE 1

Preparation of 2-methyl-2,5-dioxo-1-oxa-2-phospholane.

Use was made of a circulation reactor as shown in the drawing and described above; heatable tubular reactor 1 was 1.2 m long and 10 cm in diameter, and this reactor, the expansion vessel 3 and recycle line 4 were filled up to the overflow level in the expansion vessel 3 with an initial quantity, i.e. 10.0 liters, of crude 2-methyl-2,5-dioxo-1-oxa-2-phospholane, which was preheated to 100°-110° C and additionally heated to 140° C by means of the heater 2. 5.77 l/h (8.05 kg/h) of beta-chloroformyl-ethyl methyl phosphinic acid chloride (41.5 mol/h) at 70° C, and 4.16 l/h (4.42 kg/h) of acetic anhydride (43.2 mol) at 100° C, were continuously metered, through the lines 8 and 9 respectively, into the mixing zone 10, and from there into the base portion of the tubular reactor 1. The temperature maintained within the circulation reactor comprising the four components 1, 2, 3 and 4 was 140° C; at this temperature the starting materials reacted spontaneously to give 2-methyl-2,5-dioxo-1-oxa-2-phospholane, and acetyl chloride.

The pressure difference between the point of introduction of the mixture of starting materials into the tubular reactor 1 and the overflow level was 0.16 bar. The acetyl chloride formed ($bp_{760}$ = 51° C) was evaporated substantially completely in the expansion vessel 3. The heat which was taken out from the reactor by the evaporating acetyl chloride was replaced by heat supplied through the heater 2. The column 5, which was packed and which had a separating power corresponding to that of approximately 20 theoretical trays, served to effect the separation of the acetyl chloride. By means of the recycle line 7, a reflux ratio of 1:1 to 1:2 was maintained. 6.40 hg/h of acetyl chloride, corresponding to a yield of 95% of the theoretical, was removed through the line 12. 5.8 kg/h of the phospholane, with a purity of approximately 98%, corresponding to a yield of 99% of the theoretical, was removed through the heated pipeline 11.

The melting points of a number of specimens of this phospholane range from 98° to 100° C. Elementary analysis (wt %): $C_4H_7PO_3$ (mol. wt 134)

|  | C | H | P |
|---|---|---|---|
| Calculated: | 35.83 | 5.26 | 23.10 |
| Found: | 35.62 | 5.32 | 23.15 |

EXAMPLE 2

Preparation of 2-phenyl-2,5-dioxo-1-oxa-2-phospholane

The apparatus was as used in Example 1. The circulation reactor (components 1-4) was filled with 10 liters of crude 2-phenyl-2,5-dioxo-1-oxa-2-phospholane preheated to 120° C, and the temperature within the reactor was raised to 140° C by means of the heater 2. Next, 10.58 kg/h (42 mol/h) of beta-chloroformyl-ethyl phenyl phosphinic acid chloride preheated to 100° C, and 4.304 kg/h (42.2 mol/h) of acetic anhydride preheated to 100° C, supplied through the lines 8 and 9, respectively, were continuously metered through the mixing zone 10 into the tubular reactor 1. The pressure difference between the point of introduction of the mixture of starting materials into the reactor 1 and the overflow level in the expansion vessel 3 was 0.15 bar. THe reaction occurred as described in Example 1. There were obtained 6.15 kg/h of acetyl chloride, corresponding to a yield of 94% of the theoretical, and 8.15 kg/h of 2-phenyl-2,5-dioxo-1-oxa-2-phospholane with a purity of 98–99%, corresponding to a yield of 99% of the theoretical, this phospholane being removed through the heated pipeline 11. The melting points of a number of specimens of this phospholane ranged from 87° to 89° C. Elementary analysis (wt %): $C_9H_9PO_3$ (mol. weight 196.14)

|  | C | H | P |
|---|---|---|---|
| Calculated: | 55.11 | 4.63 | 15.79 |
| Found: | 55.04 | 4.68 | 15.68 |

We claim:

1. In a process for the continuous production of a 2,5-dioxo-1-oxa-2-phospholane of the general formula

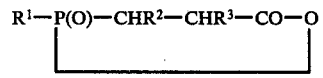

from a beta-halogenoformyl-ethyl phosphinic acid halide of the general formula

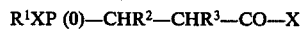

in which formulae $R^1$ stands for an alkyl radical having 1, 2, 3 or 4 carbon atoms, or a phenyl radical, $R^2$ and $R^3$ each stands for hydrogen or $CH_3$, and X stands for chlorine or bromine, by reacting the said acid halide with acetic anhydride the improvement comprises introducing, into a heatable circulation reactor, an initial quantity of the desired 2,5-dioxo-1-phospholane and circulating it therein at a temperture of 110 to 190° C; separately preheating the respective beta- halogenoformyl-ethyl phosphinic acid halide and acetic anhydride starting materials to a temperature of 60 to 160° C; mixing these starting materials together and continuously adding the resulting mixture to the material circulated in the reactor, the mixture being introduced into the lower third of the reactor; distilling off resulting acetyl halide near the head of the circulation reactor, a pressure difference of 0.1 to 5 bar being established between the point of introduction of the mixture of starting materials and the overflow level in the circulation reactor, and the material being kept circulating by the evaporating acetyl halide; and removing the resulting desired 2,5-dioxo-1-oxa-2-phospholane from the reactor at a location which is below that at which the acetyl halide is distilled off.

* * * * *